United States Patent [19]

Collins

[11] 4,170,231

[45] Oct. 9, 1979

[54] OSTOMY APPLIANCES

[75] Inventor: Michael H. Collins, Tring, England

[73] Assignee: G. D. Searle & Co., Ltd., High Wycombe, England

[21] Appl. No.: 795,681

[22] Filed: May 11, 1977

[30] Foreign Application Priority Data

May 12, 1976 [GB] United Kingdom ............... 19481/76

[51] Int. Cl.² .............................................. A61F 5/44
[52] U.S. Cl. .................................................... 128/283
[58] Field of Search ................................ 128/275, 283

[56] References Cited

U.S. PATENT DOCUMENTS

| 3,064,802 | 11/1962 | Jess et al. | 128/272 |
|---|---|---|---|
| 3,439,679 | 4/1969 | Doolittle | 128/283 |
| 3,762,412 | 10/1973 | Frank | 128/283 |
| 3,777,739 | 12/1973 | Raitto | 128/273 |
| 3,826,262 | 7/1974 | Blackwood | 128/283 |
| 4,078,567 | 3/1978 | Fenton | 128/283 |

FOREIGN PATENT DOCUMENTS 1217406 12/1970 United Kingdom .................... 128/283

Primary Examiner—Robert W. Michell
Assistant Examiner—M. Juten
Attorney, Agent, or Firm—John A. Dhuey

[57] ABSTRACT

A colostomy or ileostomy set is provided which has a substantially leakproof connection between a stoma ring and a bag or irrigation sleeve. The ostomy set includes a retaining ring which can be secured to the body of a patient, the ring having a peripheral retaining recess. A bag or irrigation sleeve has a fixing ring of size complementary to that of the retaining ring, the fixing ring having a beaded or rounded internal surface which can be removably mated with the peripheral recess of the retaining ring.

1 Claim, 5 Drawing Figures

OSTOMY APPLIANCES

This invention relates to ostomy appliances.

It is an object of the present invention to provide an improved colostomy or ileostomy set which provides a substantially leakproof connection between a stoma ring and a bag or irrigation sleeve.

According to the invention there is provided an ostomy set having a retaining ring which can be secured to the body of a patient, the said ring having a peripheral retaining recess, and a bag or irrigation sleeve which has a fixing ring of size complementary to that of the retaining ring, the said fixing ring having a beaded or rounded internal surface which can be removably mated with the peripheral recess of the retaining ring.

Figure 1:
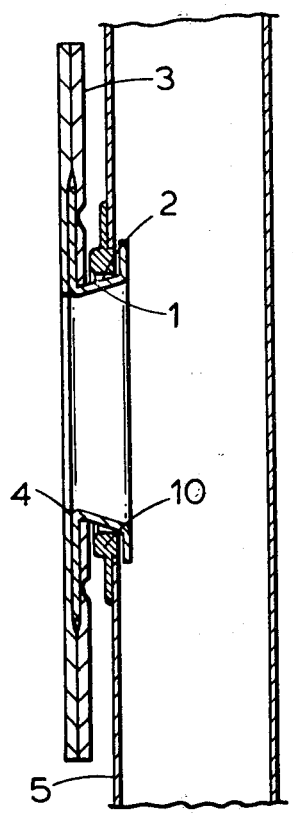
FIG. 1 is a side view showing a stoma ring and an irrigation sleeve secured thereto.

The colostomy or ileostomy set shown in FIG. 1 comprises a retaining ring 1 of semi-rigid plastics material (e.g. polyethylene) with a recess 2 in its periphery. The ring is secured by welding a sheet or disc 3, one side of which is adhesive so that the sheet can be secured to the body of a patient. The sheet has an aperture 4 of a size and shape corresponding to the internal diameter of the ring.

Figure 2:
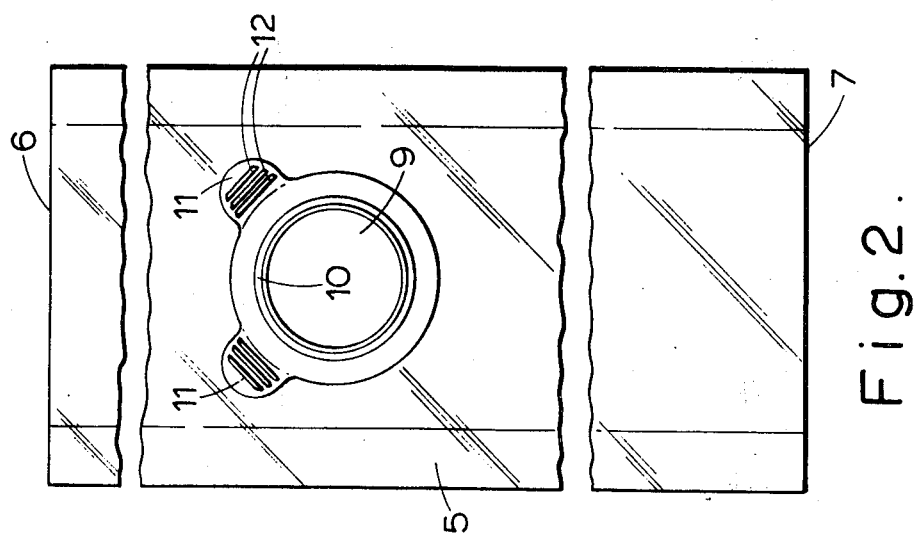
FIG. 2 is a view taken in the direction of the arrow in FIG. 1, showing the sleeve without the stoma ring.

An irrigation sleeve 5 is removably fitted to the ring 1. This irrigation sleeve is also of plastics material, for example polyvinylchloride, and has an open mouth 6 and an open bottom 7. One side of the irrigation sleeve has a fixing ring 8 welded thereto just below the open mouth of the sleeve. The fixing ring 8 surrounds an inlet aperture 9 and is of flexible plastics material, for example a polyvinylchloride having a shore hardness of 65-75. The fixing ring has a diameter corresponding to that of the retaining ring and a beaded or rounded internal surface 10 which can be engaged in the peripheral recess 2 of the retaining ring 1 to provide a substantially leakproof seal therewith. The normal diameter of the surface 10 should be from 2 to 10% smaller than the diameter of the recess 2 to provide a close fit therebetween. The fixing ring is provided with a pair of tabs 11, as shown in FIG. 2, which can be grasped by a user to assist in engaging the fixing ring on the retaining ring and disengaging it therefrom. Ridges 12 are provided on the tabs to make them easier to grasp.

Figure 3:
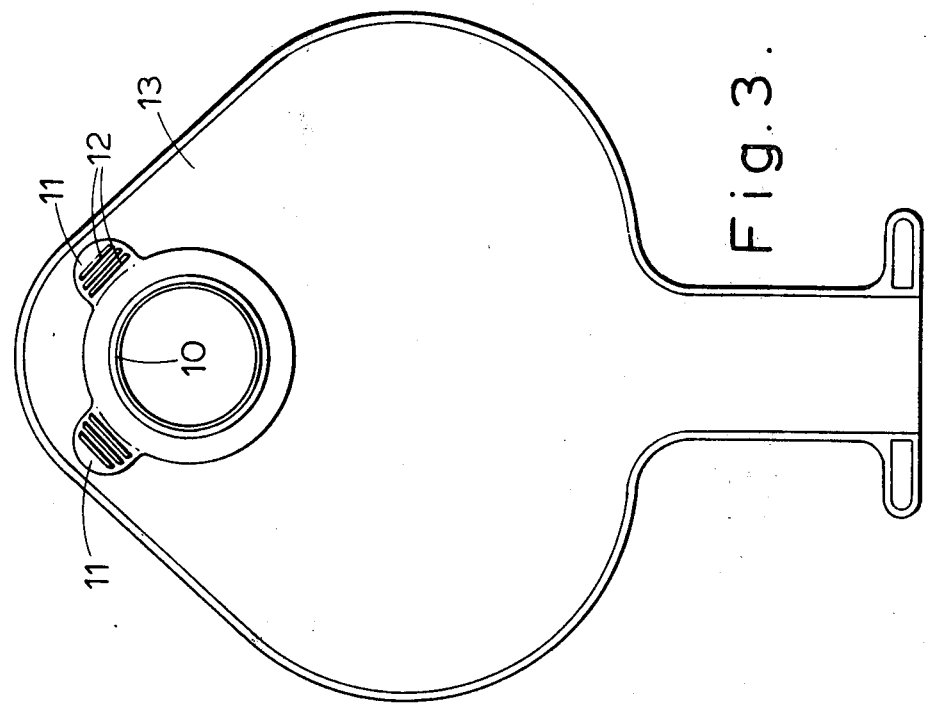
FIG. 3 is a view similar to FIG. 2 but showing a bag.

Normally a receptacle bag is fitted to the ring rather than an irrigation sleeve, and a suitable bag 13 is shown in FIG. 3. This also is provided with a fixing ring 8 identical to the fixing ring shown in FIGS. 1 and 2.

Figure 4:
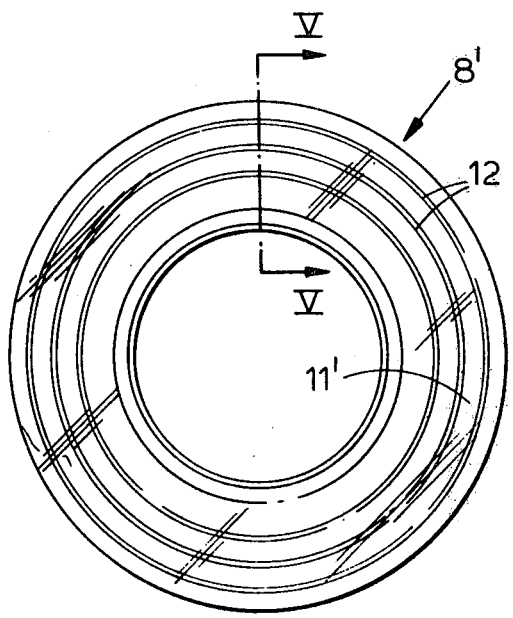
FIG. 4 shows an alternative form of fixing ring to those shown in FIGS. 1 to 3.
Figure 5:
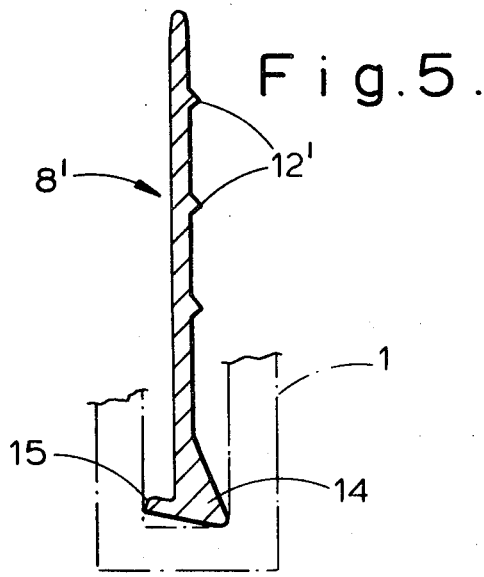
FIG. 5 is a section taken along line V—V in FIG. 4, together with a stoma ring shown in dot-dashed lines.

An alternative form of fixing ring 8' is shown in FIGS. 4 and 5. This is provided with an annular graspable surface 11' in place of the tabs 11. The surface has circular ridges 12' in place of the ridges 12. The part of the ring which engages in the recess 2 in the fixing ring has a portion 14 of generally triangular cross section which extends from one side thereof, and a lip 15 which extends from the other side thereof. This improves the seal between the rings 1 and 8', which remains substantially intact even with the flexing which the rings normally experience on the body of a wearer.

It should be appreciated that the annular graspable surface 11' may be used on a ring which has an internal surface of some shape other than that of FIG. 5, and that the internal surface shown in FIG. 5, may be used with some other forms of graspable surface, for example a plurality of tabs as shown in FIGS. 2 and 3.

When it is desired to use the irrigation sleeve 5, the receptacle bag 13 is removed from the retaining ring 1. The beaded or rounded surface 10 of the flexible fixing ring is then mated with peripheral recess 2 of the rigid retaining ring, i.e. the flexible ring is fitted over the rim of the peripheral recess in the retaining ring. The open bottom of the irrigation sleeve is conveniently placed in a lavatory pan during irrigation so that the effluent can be conducted away. When irrigation has been completed, the irrigation sleeve is removed and replaced by a receptacle bag.

Other accessories may be attached to the retaining ring in place of the irrigation sleeve and receptacle bag. For example a cap may be attached when the patient wishes temporarily to be as unencumbered as possible, such as when engaged in a sport. Another accessory which may be attached is a cap provided with a drain tube leading to a bag at a distance therefrom. This is convenient for use when the patient is sleeping. The bag may then be placed outside the bed and there is no risk of the patient lying on it. These accessories will, of course, have their own fixing rings for engagement with the retaining ring.

I claim:

1. An ostomy set having a retaining ring which can be secured to the body of a patient, said ring having a peripheral retaining recess formed by a front wall, a bottom wall and a back wall, said front wall and said back wall having inner, opposed planar surfaces, and a bag or irrigation sleeve which has a fixing ring of a size complementary to that of the retaining ring, said fixing ring having an internal surface with a bead extending from one face thereof and a lip extending from the opposite face thereof, said bead and said lip simultaneously engaging said opposed inner surfaces of said front and back walls of said retaining ring, and said bead having a generally triangular cross section which is greater than the cross section of said lip.

* * * * *